United States Patent [19]
Malchesky

[11] Patent Number: 5,747,794
[45] Date of Patent: May 5, 1998

[54] SCANNING DEVICE FOR EVALUATING CLEANLINESS AND INTEGRITY OF MEDICAL AND DENTAL INSTRUMENTS

[75] Inventor: Paul S. Malchesky, Painesville Township, Ohio

[73] Assignee: Steris Corporation, Mentor, Ohio

[21] Appl. No.: 732,038

[22] Filed: Oct. 16, 1996

[51] Int. Cl.$^6$ .................................................. H01J 5/16
[52] U.S. Cl. ........................ 250/227.23; 250/227.11; 356/241
[58] Field of Search ............. 250/227.11, 227.14, 250/227.18, 227.29, 227.3, 227.31, 227.32, 310, 227.23; 356/241; 128/655, 665, 632–634; 385/12, 5, 2, 8

[56] References Cited

U.S. PATENT DOCUMENTS

| | | | |
|---|---|---|---|
| 4,559,813 | 12/1985 | Brekelmans | 250/227.11 |
| 4,892,706 | 1/1990 | Kralovic et al. | 422/28 |
| 5,217,698 | 6/1993 | Siegel et al. | 422/295 |
| 5,219,345 | 6/1993 | Potter | 250/227.11 |
| 5,233,203 | 8/1993 | Haga | |
| 5,245,403 | 9/1993 | Kato et al. | 356/237 |
| 5,479,252 | 12/1995 | Worster et al. | 356/237 |
| 5,481,109 | 1/1996 | Ninomiya et al. | 250/310 |

FOREIGN PATENT DOCUMENTS

| | | |
|---|---|---|
| 493815 | 10/1992 | European Pat. Off. |
| 7159331 | 6/1995 | Japan |
| 1803841 | 3/1993 | U.S.S.R. |

OTHER PUBLICATIONS

"Surface Analysis of Clinically–Used Expanded PTFE Endoscopic Tubing Treated By the STERIS Process", Tucker, et al., ASAIO Journal, 1995 Abstracts, 41st Annual Conference May 4–6, 1995 p. 17.

"Surface Analysis of Clinically–Used Expanded PTFE Endoscopic Tubing Treated By the STERIS Process", Tucker, et al., ASAIO Journal 1996, May 10, 1996, pp. 001–008.

"Predicting Technology Advances for Wafer Surface Inspection Systems", Pirooz, et al., Microcontamination V. 11, No. 10, Nov. 1993, (Abstract Only).

"Laser Induced Infrared Signature: The Stepping Stone to Statistical Process Control for PTH, SMT, FPT, AND TAB", Vanzetti, et al., 3rd Int. SAMPE Electronics Conference, Los Angeles, CA Jun. 20, 1989, (Abstract Only).

"Contamination Control For the MSX: An Overview", Cranmer, et al. Johns Hopkins APL Technical Digest, vol. 17, No. 1, 1996, (Abstract Only).

"Reconvergent Specular Detection of Material Defects on Silicon", Ferrara, et al., IEEE/SEMI 1995, ASMC '95 Proceedings, Jan. 1995 (Abstract Only).

"Using an Advanced Particle Analysis System for Process Improvement", Uritsky, et al., Microcontamination, vo. 12, No. 5, May 1994, (Abstract Only).

(List continued on next page.)

*Primary Examiner*—Que Le
*Attorney, Agent, or Firm*—Fay, Sharpe, Beall, Fagan, Minnich & McKee

[57] ABSTRACT

Medical and other instruments and devices (16, 44) may have a build-up of biological residue film, even after sterilizing. Dead cell membranes in this film can give off endotoxins. To check for the presence of biological residue film, light from a source (10, 40) travels along optical fibers (12, 42) and is focused by a lens (24) on a surface (26) to be examined. Reflected or transmitted light is conveyed by optical fibers (46) to an opto-electrical analyzing device (30, 48). In one embodiment, the opto-electrical device (30) senses the intensity of reflected light to provide an indication of reflectivity attributable to the biological film build-up. In another embodiment, a spectrophotometer (48) converts the returned light into an indication of the reflected spectrum which is analyzed (50) to determine the nature of the material which reflected the light, in particular the type of protein or other biological residue found on the examined surface.

18 Claims, 3 Drawing Sheets

OTHER PUBLICATIONS

"NIR For Noncontact Measurement of Moisture and Protein Content", Scott, Sensor Review, vol. 11, No. 4, 1991, Jan. 1991, (Abstract Only).

"A New Stereo Laser Triangulation Device for Specular Surface Inspection", Samson, et al., Proceedings of the SPIE, vol. 1332, Pt. 1, 1990, (Abstract Only), Jan. 1990.

"Particle–Detection on Glass Substrates and Thin Film Magnetic Storage Disks", Lenhart, IEEE Trans. on Magnetics, vol. 26, No. 1, 1990, Jan. 1990, (Abstract Only).

"Total Internal Reflection Microscopy: A Surface Inspection Technique", Temple, Applied Optics, vol. 20, No. 15, 1981, Jan. 1981. (Abstract Only).

"Contamination Detection NDE for Cleaning Process Inspection", NASA Marshall Space Flight Center, Aerospace Env. Technology Conference, Mar. 1995, (Abstract Only).

"Surface Contamination Analysis Technology Team Overview", NASA Marshall Space Flight Center, Aerospace Env. Technology Conference, Mar. 1995, (Abstract Only), "How Clean is Clean: Non–Destructive/Direct Methods of Flux, Residue Detection", Welsh, et al., Dept. of Energy, International Conference on Solder Fluxes and Pastes, Jun. 1994, (Abstract Only).

"Resolution of Contamination Problems Affecting Laser–Surface–Certification Inspection", Jackson, Dept. of Energy, Mar. 1982, (Abstract Only).

SCANNING DEVICE FOR EVALUATING CLEANLINESS AND INTEGRITY OF MEDICAL AND DENTAL INSTRUMENTS

BACKGROUND OF THE INVENTION

The present invention relates to the cleaning, sanitizing, disinfecting, and sterilization arts. It finds particular application in conjunction with the sterilization of endoscopes and will be described with particular reference thereto. However, it is to be appreciated that the present invention is also applicable to a wide variety of medical, dental, surgical, mortuary, veterinary, industrial, and other areas in which potentially hazardous microbes are removed from devices.

Heretofore, instruments and devices which are used in various medical, dental, surgical, veterinary, and industrial processes are sterilized, disinfected, or at least sanitized before use. Typically, these instruments or devices have been rinsed in water, such as deionized water, saline solution, or tap water, to remove organic residue after use. Frequently, biological materials, e.g., proteins, blood, mucous, and polysaccarides, formed a film which remained on the instruments or devices after rinsing. This film built-up particularly in hard to access places such as in the channels of an endoscope.

After rinsing, the devices were typically disinfected or sterilized using one of a variety of techniques. Typical techniques included steam sterilization in which the instrument or device was heated to a high temperature and pressure in the presence of steam to kill harmful microorganisms. Any microorganisms on the instrument or in the biological residue were killed during steam sterilization. The residue film was typically baked on to the instrument. However, because the baked on residue was sterilized, the residue was not generally considered to be a concern.

Other instruments, particularly those which were not able to take the temperature and pressure of steam sterilization were disinfected or sterilized with other techniques. Some were immersed in glutaraldehyde, a high level disinfectant. The glutaraldehyde tends to blacken the protein film. Other instruments were treated with ethylene oxide gas, which again killed the living organisms in the biological residue.

Instruments that are treated with a flowing liquid sterilant or disinfectant, such as that shown in U.S. Pat. Nos. 4,892,706 and 5,217,698 normally have the residue removed. The flowing liquid included not only a strong oxidant such as peracetic acid, but also a wetting agent or detergent and water which helped to dissolve and remove the biological residue. See also, "Surface Analysis of Clinically-Used Expanded PTFE Endoscopic Tubing Treated By the STERIS Process", Tucker, et al. ASAIO Journal, 1995 Abstracts, 41st Annual Conference May 4-6, 1995, p. 17, and "Surface Analysis of Clinically-Used Expanded PTFE Endoscopic Tubing Treated By the STERIS Process", Tucker, et al. ASAIO Journal 1996, May 10, 1996, pp. 001-008.

The techniques which kill living microorganisms in the biological residue left on the device have several drawbacks. First, some people find the use of instruments which carry even sterile biological residue from former patients to be objectionable. Residuals may affect the performance of the device as it was intended to be used. Second and more importantly, it has now been found that the sterilized residue are not necessarily safe. When the microorganisms are killed, the membranes of the dead cells remain. These membranes contain pyrogens and give off endotoxins as the cell walls break down. Thus, even the dead cells remaining after sterilization can be toxic.

In accordance with the present invention, a method and apparatus are provided for checking for the presence of biological residue in sanitized, disinfected, or sterilized instruments and devices.

SUMMARY OF THE INVENTION

In accordance with one aspect of the present invention, an apparatus is provided for inspecting devices and instruments for biological residue. A light source provides illumination and conveys the illumination along a transmission light path to a surface to be examined. An opto-electric circuit receives light from the examined surface and converts the received light into an electrical signal indicative thereof. A display receives the electrical signal and provides a human-readable display indicative of any presence of biological residue on the examined surface.

In accordance with a more limited aspect of the present invention, optical fibers extend along the transmission light path and along a received light path for guiding light from the light source to the examined surface and from the examined surface to the opto-electrical circuit.

In accordance with another more limited aspect of the present invention, the opto-electrical circuit converts the received light into a signal indicative of the intensity of the received light.

In accordance with another more limited aspect of the present invention, the opto-electrical circuit includes a spectrophotometer for producing a signal indicative of a spectrum of received light. A spectrum comparator compares electronically the spectrum from the spectrophotometer with a plurality of spectra characteristic of a plurality of biological residue materials to identify a nature of any biological material residue.

In accordance with another aspect of the present invention, a method of examining an instrument or device for biological build-up is provided. Light is transmitted along a transmission light path to a surface of an instrument or device to be examined. Light received from the examined surface is analyzed to determine residue characteristics of the examined surface. A display indicative of the characteristics of the examined surface is provided.

In accordance with a more limited aspect of the present invention, the transmitted light has a pre-selected spectrum.

In accordance with a more limited aspect of the present invention, a spectrum of the received light is determined. The determined spectrum is compared with spectra of known biological residue material. In accordance with the comparison, a determination is made of a type of biological material on the examined surface.

In accordance with another more limited aspect of the present invention, an intensity of the received light is determined and converted into an indication of a relative amount of biological residue.

In accordance with another more limited aspect of the present invention, the light from the light source is reflected or transmitted from the examined surface.

One advantage of the present invention is that it monitors for the removal of biological residue film.

Another advantage of the present invention is that it is amenable for use with instruments and devices with hard to reach regions.

Another advantage of the present invention resides in its simplicity and ease of use.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
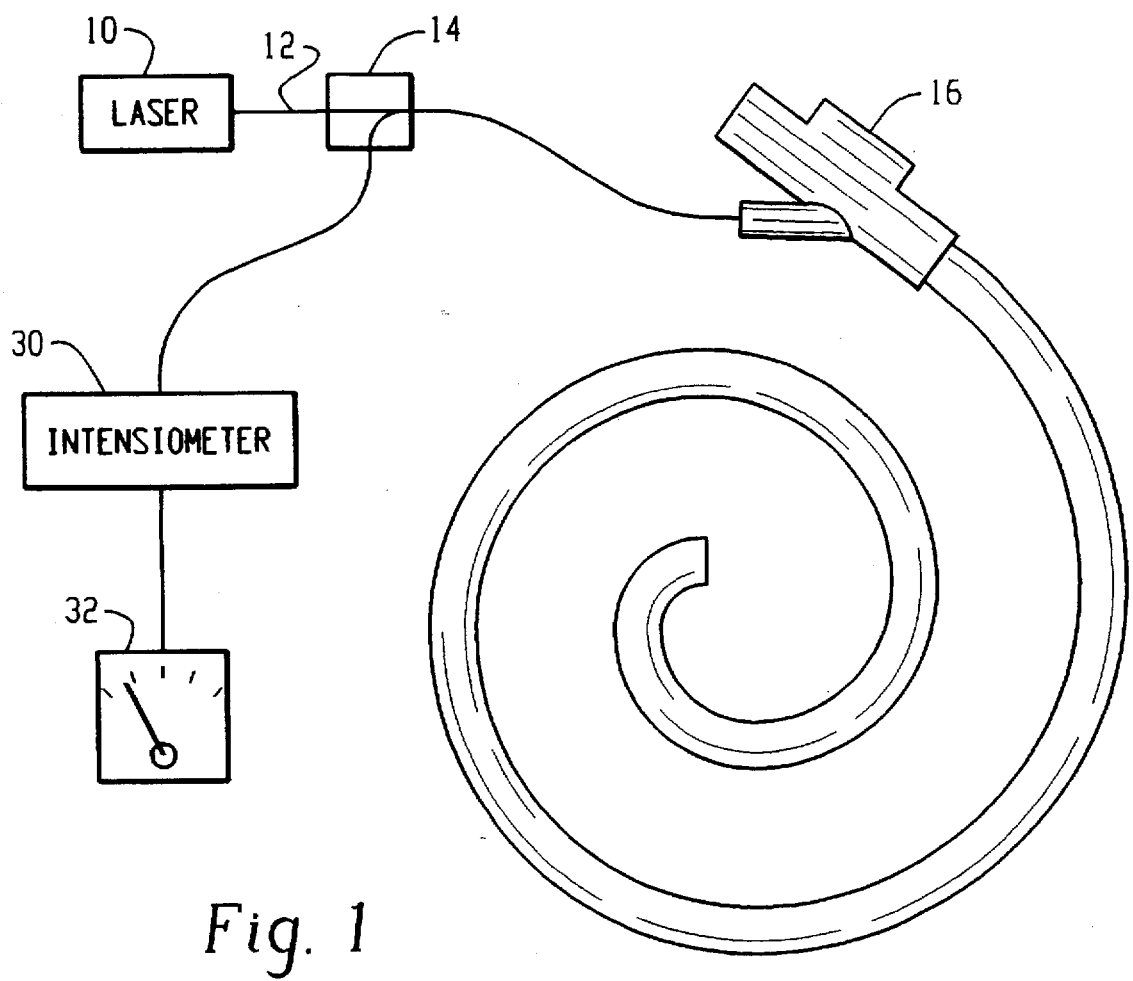
FIG. 1 is a diagrammatic illustration of an inspection device in accordance with the present invention.

With reference to FIG. 1, a source of light such as a laser 10 outputs light such as from the infrared (IR), near infrared, or visible region of the light spectrum along an optical fiber 12 or other light guide. The optical fiber extends through a beam splitter 14 and to a device or instrument 16 to be examined. In the illustrated embodiment, the end of the optical fiber is received within an internal channel of an endoscope.

Figure 2:
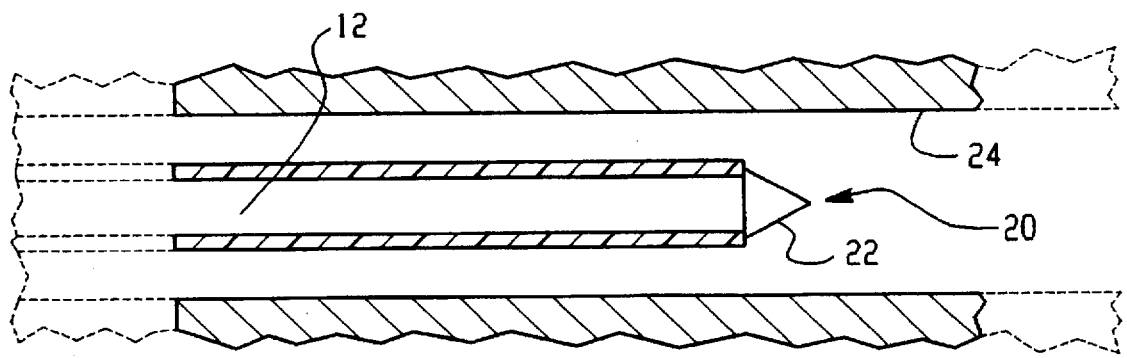
FIG. 2 is a detailed drawing of an end of the optic fiber probe.

With reference to FIG. 2, the optical fiber 12 which extends into the device has a lens arrangement 20 connected to its end. In the illustrated embodiment, the lens arrangement includes an optical element 22 such as a prism, which deflects the light from along an axis of the channel towards adjacent walls 24 and light from adjacent walls back along the optical fiber. The reflected light is focused to travel along the optic fiber 12 in the opposite direction until it reaches the beam splitter 14, where it is directed to an opto-electric transducer 30 which converts the light to an electrical signal. The electrical signal is related to the interaction of the absorbed material (biological or other) on device and light absorption. In the illustrated embodiment, the opto-electric transducer includes an intensiometer which converts the reflected light into an electrical signal proportional to its intensity. An indicator, such as a gauge 32 provides a visual output proportional to the intensity of the reflected light.

In one embodiment, the light source transmits light of a wavelength, such as infrared, which is absorbed differently by the device and the residual materials. A change in the relative amounts of light reflected and absorbed is indicative of the residual material build-up.

In another embodiment, the surface 24 being inspected is constructed of or coated with a white or other light color coating. Any biological residue remaining after detergent washing darkens or blackens with glutaraldehyde reducing the intensity of reflected light. In this manner, the relative amount of reflected light indicated by the display 32 is indicative of the presence and even the amount of built-up biological residue.

Figure 3:
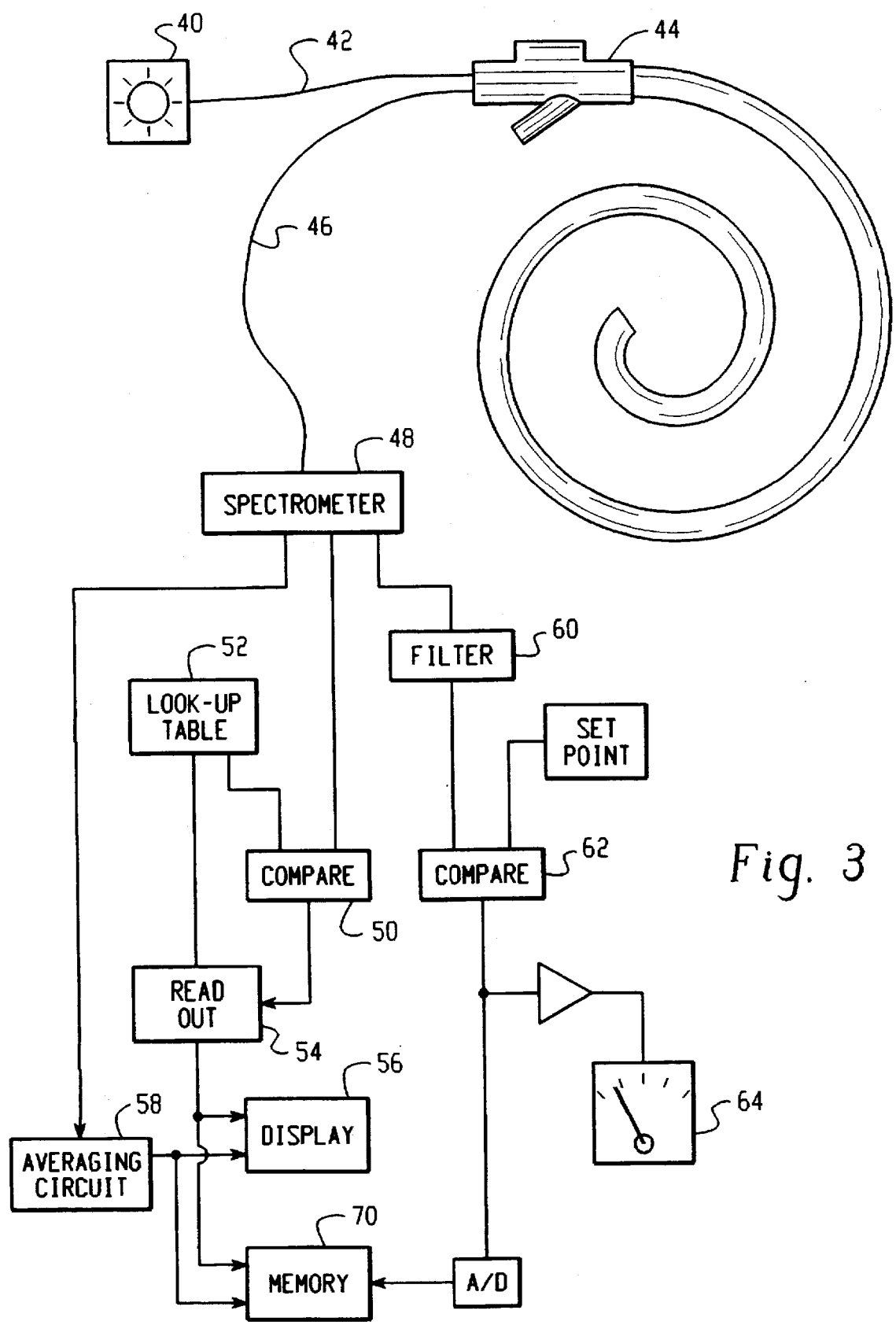
FIG. 3 is an alternate embodiment of the inspection device of FIG. 1.

In the embodiment of FIG. 3, a polychromatic light source 40 sends light along a light guide such as fiber optic bundle 42. The light is emitted at the end of the fiber optic bundle and is reflected off an examined surface, e.g., an interior channel of a diagnostic instrument or device 44. A second fiber optic bundle which runs parallel to, surrounds, or is surrounded by the fiber optic bundle 42 receives the reflected light and conveys it to a spectrophotometer 48. Alternately, for transparent walls, the transmission and return light guides are positioned on opposite sides of the wall to means transmitted light. The spectrophotometer 48 produces an output electrical signal indicative of intensity as a function of wavelength. That is, the spectrum of the reflected light including the relative intensity of the reflected light at each of a plurality of characteristic wavelengths is output by the spectrophotometer.

Typically, each molecule (i.e., protein) has a characteristic spectra or curve of intensity versus wavelength. A spectrum comparer 50 electronically compares the output spectrum with each of a plurality of spectrum indicative of known proteins or substances stored in a look-up table 52. A memory reading circuit 54 reads out of the look-up table 52 the name or other identification of the protein or substance whose spectra most closely matches the spectra received from the spectrophotometer 48. A display 56 provides a display of the protein or proteins whose spectra are found within the instrument. An averaging circuit 58 calculates a weighted average of the spectra to provide an indication of the intensity of the related light to provide an indication of the relative magnitude of the output signal. The weighted averaging circuit 58 is also connected with the display 56 to provide an indication of a level of residue build-up.

Optionally, rather than determining the exact nature of the protein, a filter 60 filters the resultant spectra such that only the intensity(ies) corresponding to one or a selected number of wavelengths or bands is passed to a comparator 62. The comparator 62 compares the magnitude with a set point to determine a relative amount of residue film. The relative amount of residue film is displayed on a display 64 to provide an indication of relative cleanliness.

Another way to analyze the surface is to monitor for the chemical composition of the materials of which the device is constructed. A decay in this signal versus control, not contaminated sample of the material, is an indication of a residue build-up. The residue can be biological, chemical, such as a residue from detergents or washing chemicals.

Optionally, each device or instrument can be coded with a preselected code, such as a bar code. A bar code reader can be incorporated into the same physical housing or another housing to read the identification of the instrument or device. The identification of the instrument along with the information displayed on the output display are preferably conveyed to a memory 70 which records the identification of the instrument, the examination results, and the date and time of the examination.

The fiber optic probe is convenient when measuring reflected light from within channels and deep recesses. However, it is to be appreciated that the optical fibers may be eliminated in favor of a lens mounted directly on the light source and a photo pickup for reflected or transmitted light mounted behind or adjacent to the lens.

Figure 4:
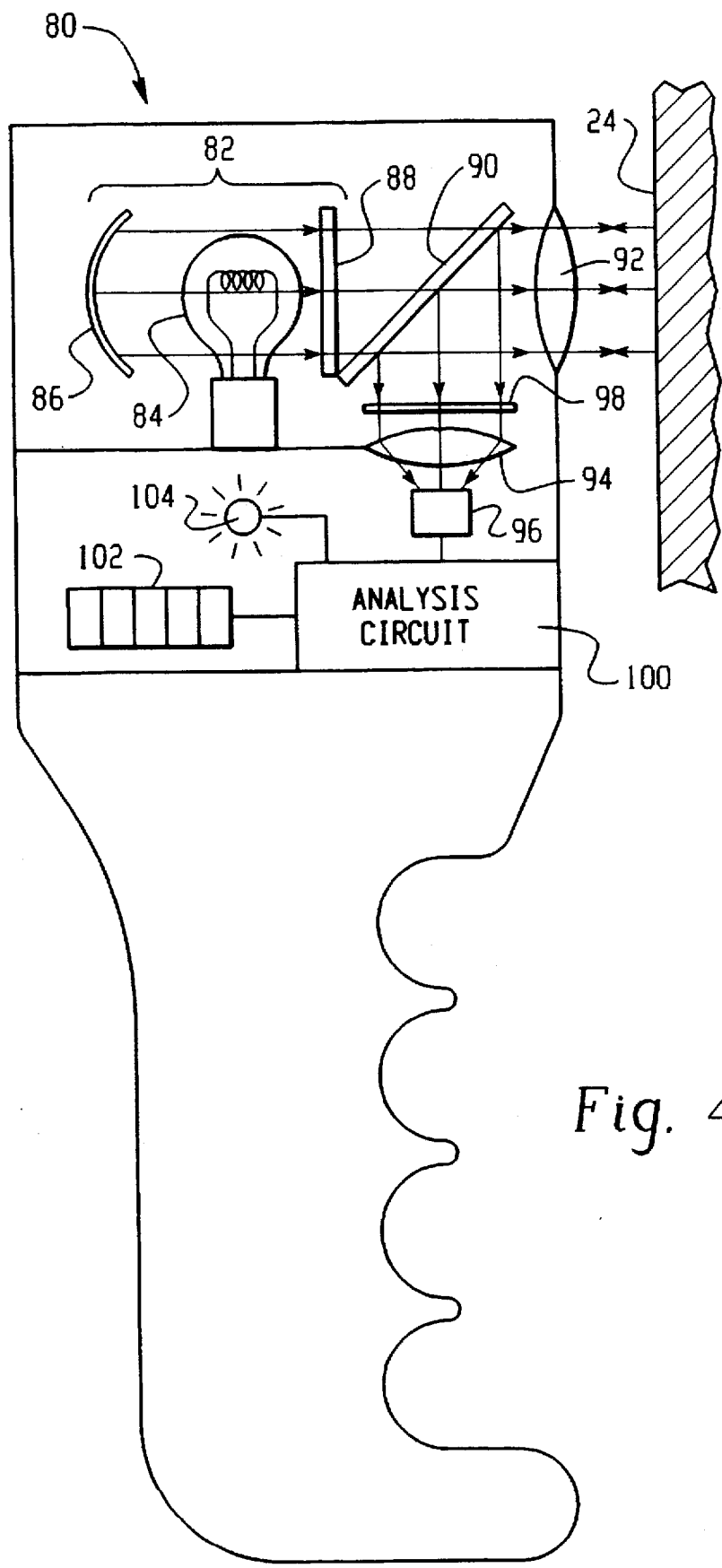
FIG. 4 is another alternate embodiment of the inspection device of FIG. 1.

In the embodiment of FIG. 4, a hand-held unit 80 is swept over a surface 24 for residue. An illumination source 82, such as a light bulb 84, a reflector 86, and a spectral filter 88, generate light with a preselected spectrum. In the illustrated embodiment, the light passes through a half-silvered mirror 90 and a lens 92, for striking the surface 24. Light reflected from the surface passes back through lens 92 and is reflected by the half-silvered mirror 90 to a lens 94 which focuses the reflected light on an optical sensor 96. Optionally, a spectral filter 98 limits the reflected light to preselected components. An analysis circuit 100 analyzes the received light to determine the amount of residue, the nature of the residue, or the like. In a preferred embodiment, the analysis circuit includes a memory which stores a reference reflected intensity. The hand-held scanner is scanned over a clean, residue free portion of a reference instrument to obtain a reference value for storage in the memory. Thereafter, as the scanner is scanned over surfaces to be analyzed, a comparitor compares the stored reference value with the current value to determine an amount of contamination. Optionally, any of the analysis techniques discussed above or their equivalents can also be utilized. Based on the analysis, a numeric or alphanumeric display 102 advises the operator of the amount and nature of the residue. Optionally, an indicator light 104 is illuminated in response to the amount of detected residue exceeding a preselected residue limit.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for inspecting devices and instruments for residues, the apparatus comprising:

a light source which provides illumination, conveys the illumination along a transmission light path, and illuminates a surface to be examined;

a spectrophotometer which receives light reflected from the examined surface, spectrally analyses the reflected light, and produces a signal indicative of a spectrum of the reflected light.

2. The apparatus as set forth in claim 1, further including a display which receives the signal and provides a human-readable display indicative of any presence of residues on the examined surface.

3. The apparatus as set forth in claim 1 further including optical fibers extending along the transmission light path and a received light path for guiding light from the light source to the examined surface and from the examined surface to the spectrophotometer.

4. The apparatus as set forth in claim 2 further including:

a filter which passes only signal components corresponding to selected wavelengths of light;

a comparator which compares the signal passed through the filter with a set point, the comparator being connected with the display.

5. The apparatus as set forth in claim 1 further including:

optical fibers extending along the transmission light path and a reflected light path;

an optical element connected with ends of the optical fibers adjacent the examined surface for focusing transmitted light from the optical fibers onto the examined surface and for focusing reflected light from the examined surface back into the optical fibers.

6. An apparatus for inspecting devices and instruments for residues, the apparatus comprising:

a light source which provides illumination, conveys the illumination along a transmission light path, and illuminates a surface to be examined;

an opto-electric circuit which receives light from the examined surface, spectrally analyses the received light and determines a spectrum of the received light;

a spectrum comparator which compares electronically the spectrum from the opto-electric device with spectra characteristic of a plurality of residues to determine the nature of any residues;

a display connected with the spectrum comparator which provides a human-readable display indicative of any presence of residues on the examined surface and the nature of the residues.

7. The apparatus as set forth in claim 6 further including a recorder for recording results of the spectrum comparison along with an identification of the examined device or instrument.

8. An apparatus for inspecting devices and instruments for residues, the apparatus comprising:

a light source;

optical fibers extending along a transmission light path from the light source to terminal ends of the fibers adjacent a surface to be examined to transmit light to the examined surface and extending along a reflected light path to convey reflected light from the examined surface therealong;

a prism disposed adjacent the terminal ends of the optical fibers for reflecting the transmitted light in a direction transverse to a central axis of the optical fibers onto the examined surface and for directing the reflected light from the examined surface back into the optical fibers;

an opto-electric circuit connected to the optical fibers to receive the light reflected from the examined surface, the opto-electric device converting the received light into an electrical signal indicative thereof.

9. A method of examining a medical instrument or device for residue material build-up, the method comprising:

transmitting light along a transmission light path to a surface of the instrument or device to be examined;

analyzing light reflected from the examined surface by:

selecting one or more predetermined wavelengths;

comparing an intensity of each selected wavelength with a corresponding preselected set point; and from the comparison, determining a cleanliness of the examined surface.

10. The method of examining an instrument or device for residue material build-up as set forth in claim 9 further including:

providing a display indicative of the type of residue material on the examined surface.

11. A method of examining an instrument or device for residue material build-up, the method comprising:

transmitting light along a transmission light path to a surface of the instrument or device to be examined;

analyzing light received from the examined surface to determine a type of residue material on the examined surface including:

determining a spectrum of the received light;

comparing the spectrum with spectra of known residue materials;

in accordance with the comparison, making a determination of the type of residue material on the examined surface.

12. The method as set forth in claim 11 wherein the plurality of known spectra include the spectra for proteins and biological materials.

13. The method as set forth in claim 11 wherein the analyzing further includes:

determining an intensity of the received light and converting the determined intensity into an indication of a relative amount of the residue material on the examined surface.

14. The method as set forth in claim 11 further including after the transmitting step and before the analyzing step:

reflecting the transmitted light from the examined surface;

conveying the reflected light away from the examined surface along an optical fiber light path for analysis.

15. A method of detecting cleanliness of a medical instrument or device for residue material build-up, the method comprising:

transmitting light along a transmission light path to a surface of the instrument or device to be examined;

analyzing light reflected from the examined surface to determine residue characteristics of the examined surface, the analyzing step including:

analyzing the reflected light to determine characteristics thereof;

comparing the determined characteristics with characteristics of light reflected from at least one reference material; and, providing a display indicative of the characteristics of the comparison.

16. The method as set forth in claim 15 wherein the at least one reference material includes a material of which the instrument or device is at least partially constructed.

17. The method as set forth in claim 15 wherein the at least one reference material is a biological material.

18. A method of monitoring the interior of a lumen for residue material build-up, the method comprising:

transmitting light along an optical fiber extending through the interior of the lumen to be examined;

reflecting the light transmitted along the optical fiber from at least one examined surface region of the lumen interior;

analyzing the light reflected from the at least one lumen interior surface region to determine residue characteristics of the examined lumen interior surface region;

providing a display indicative of the cleanliness of the examined lumen interior surface region.

* * * * *